(12) United States Patent
Jain et al.

(10) Patent No.: US 12,727,772 B2
(45) Date of Patent: Sep. 8, 2026

(54) STRETCHABLE BLOOD PRESSURE CUFF

(71) Applicant: Apple Inc., Cupertino, CA (US)

(72) Inventors: Pranay Jain, Cambridge, MA (US); Nicholas R. Trincia, San Francisco, CA (US); Chia-Hsien Lin, Glendale, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 1084 days.

(21) Appl. No.: 17/210,371

(22) Filed: Mar. 23, 2021

(65) Prior Publication Data

US 2021/0321889 A1 Oct. 21, 2021

Related U.S. Application Data

(60) Provisional application No. 63/011,061, filed on Apr. 16, 2020.

(51) Int. Cl.
*A61B 5/022* (2006.01)
*A61B 5/00* (2006.01)
*A61B 5/0235* (2006.01)

(52) U.S. Cl.
CPC ........ *A61B 5/02233* (2013.01); *A61B 5/0235* (2013.01); *A61B 5/6824* (2013.01); *A61B 2560/04* (2013.01)

(58) Field of Classification Search
CPC . A61B 5/02233; A61B 5/0235; A61B 5/6824; A61B 2560/04
See application file for complete search history.

(56) References Cited

U.S. PATENT DOCUMENTS 4,005,701 A 2/1977 Aisenberg et al.
4,290,434 A 9/1981 Jewett
(Continued)

FOREIGN PATENT DOCUMENTS

CN 103598879 2/2014
CN 104545892 4/2015
(Continued)

OTHER PUBLICATIONS

U.S. Appl. No. 17/354,775, filed Jun. 22, 2021, Montgomery II et al.
(Continued)

*Primary Examiner* — Justin Xu
(74) *Attorney, Agent, or Firm* — Brownstein Hyatt Farber Schreck, LLP

(57) ABSTRACT

Embodiments include a blood pressure measurement device that includes a cuff for measuring blood pressure of a user. The cuff may include a bladder assembly configured to retain a fluid within an internal chamber where the bladder assembly is formed from a first cell defining a first portion of the internal chamber that is connected with a second cell defining a second portion of the internal chamber. The bladder assembly can also include a fluid passage that is in fluid communication with the first cell and the second cell and coupled with a reservoir. The bladder assembly can exchange the fluid with the reservoir and be configured to increase in length when a volume of the fluid in the internal chamber decreases, and decrease in length when the volume of the fluid in the internal chamber increases.

20 Claims, 13 Drawing Sheets

(56) References Cited

U.S. PATENT DOCUMENTS 4,548,198 A 10/1985 Manes
4,896,676 A 1/1990 Sasaki
5,135,003 A 8/1992 Souma
5,403,268 A 4/1995 Clement
5,494,043 A 2/1996 O'Sullivan
5,620,001 A 4/1997 Byrd et al.
5,632,278 A 5/1997 Rometsch
5,666,404 A 9/1997 Ciccotelli et al.
6,162,181 A 12/2000 Hynson et al.
6,251,080 B1 6/2001 Henkin et al.
6,364,843 B1 4/2002 Lightle
6,497,668 B2 12/2002 Nishibayashi
6,689,069 B2 2/2004 Bratteli et al.
6,694,821 B2 2/2004 Yamakoshi et al.
6,705,998 B2 3/2004 Stergiopoulos et al.
6,814,077 B1 11/2004 Eistert
6,988,992 B2 1/2006 Just et al.
7,111,625 B2 9/2006 Jackson
7,678,059 B2 3/2010 Friedman et al.
7,927,283 B2 4/2011 Riobo Aboy
8,690,799 B2 4/2014 Telfort et al.
8,747,328 B2 6/2014 Tichauer
8,911,378 B2 12/2014 Whitaker et al.
8,998,817 B2 4/2015 Pfeiffer et al.
9,192,351 B1 11/2015 Telfort et al.
9,198,584 B2 12/2015 Yamashita et al.
9,474,485 B2 10/2016 Sato
9,723,985 B2 8/2017 Ono et al.
9,781,984 B2 10/2017 Baranski et al.
9,986,919 B2 6/2018 Lamego et al.
10,064,561 B2 9/2018 Kinoshita et al.
10,349,841 B2 7/2019 Li
10,405,806 B2 9/2019 Baik et al.
10,502,328 B2 12/2019 Kotani et al.
10,758,130 B2 9/2020 Mullin
10,874,307 B2 12/2020 Narasimhan et al.
11,134,901 B2 10/2021 Fine et al.
11,172,839 B2 11/2021 Ward et al.
11,179,049 B2 11/2021 Niehaus et al.
11,298,032 B2 4/2022 Mou et al.
11,439,531 B2 9/2022 Goel
11,576,583 B2 2/2023 Dana et al.
12,138,023 B2 11/2024 Nishida et al.
2002/0143259 A1 10/2002 Stergiopoulos et al.
2004/0044288 A1 3/2004 Gorenberg et al.
2004/0049114 A1 3/2004 Alesse
2004/0199081 A1 10/2004 Freund et al.
2006/0111637 A1 5/2006 Jacober et al.
2007/0185402 A1 8/2007 Yang et al.
2007/0203416 A1 8/2007 Lowe
2009/0012411 A1 1/2009 Lowe et al.
2009/0156946 A1 6/2009 Lane et al.
2010/0106029 A1 4/2010 Fraden
2010/0113943 A1 5/2010 Burnes et al.
2010/0186752 A1 7/2010 Rixson
2011/0040197 A1 2/2011 Welch et al.
2011/0066046 A1 3/2011 Young et al.
2012/0136262 A1 5/2012 Sawanoi et al.
2012/0209129 A1 8/2012 Smith et al.
2012/0238887 A1 9/2012 Gerdt et al.
2012/0316448 A1 12/2012 Gu
2012/0330112 A1 12/2012 Lamego et al.
2013/0053707 A1 2/2013 Mirisoloff
2013/0060147 A1 3/2013 Welch et al.
2013/0144176 A1 6/2013 Lec
2013/0150736 A1 6/2013 Romano
2014/0187987 A1 7/2014 Fraden et al.
2014/0309541 A1 10/2014 Yamashita et al.
2015/0105675 A1 4/2015 Nakagawa et al.
2015/0157223 A1 6/2015 Pollyea
2015/0182130 A1 7/2015 Utter
2015/0351851 A1 12/2015 Deselle
2016/0000508 A1 1/2016 Finn
2016/0038044 A1 2/2016 Banerjee et al.
2016/0106326 A1 4/2016 Bajaj et al.
2016/0120418 A1 5/2016 Oksala et al.
2017/0042433 A1 2/2017 Noh et al.
2017/0164876 A1 6/2017 Hyde
2017/0224357 A1* 8/2017 Whalen ................ A61B 17/135
2017/0231512 A1 8/2017 Li
2017/0238819 A1 8/2017 Waller et al.
2017/0273579 A1 9/2017 Mori et al.
2017/0290519 A1 10/2017 Zhou
2017/0352695 A1 12/2017 Tsuchiya
2018/0092553 A1 4/2018 Baumbach et al.
2018/0098897 A1 4/2018 Lundh et al.
2018/0116607 A1 5/2018 Yu et al.
2018/0153418 A1* 6/2018 Sullivan ............. A61B 5/02233
2018/0177411 A1 6/2018 Du et al.
2018/0184920 A1 7/2018 Rabinovich et al.
2018/0184924 A1 7/2018 McMillan
2018/0338693 A1 11/2018 Li et al.
2019/0099092 A1 4/2019 Zhang et al.
2019/0133455 A1 5/2019 Mou et al.
2019/0261870 A1 8/2019 Nishikawa
2019/0290143 A1 9/2019 Iwata et al.
2020/0008691 A1 1/2020 Obayashi et al.
2020/0054221 A1 2/2020 Ward et al.
2020/0129078 A1 4/2020 Kanegae et al.
2020/0138303 A1 5/2020 Jafari et al.
2020/0196883 A1 6/2020 Matsumoto et al.
2020/0232634 A1 7/2020 Sharrah
2020/0323446 A1 10/2020 Nishida et al.
2021/0030372 A1 2/2021 Lizio et al.
2021/0059537 A1 3/2021 Nakagawa et al.
2021/0127993 A1 5/2021 Matsumura et al.
2021/0169347 A1 6/2021 Ito et al.
2021/0236012 A1 8/2021 Nishida et al.
2021/0251499 A1 8/2021 Ogawa
2021/0285436 A1 9/2021 Fukami
2021/0307627 A1* 10/2021 Taniguchi ........... A61B 5/6824
2021/0378529 A1 12/2021 Colburn
2022/0000380 A1 1/2022 Li et al.
2022/0015652 A1 1/2022 Lee et al.
2022/0054020 A1 2/2022 Tadele et al.
2022/0087545 A1 3/2022 Jain et al.
2022/0240803 A1 8/2022 Han et al.
2022/0400959 A1 12/2022 Montgomery et al.
2023/0063813 A1 3/2023 Smith et al.
2023/0068620 A1 3/2023 Tadele et al.
2023/0355991 A1 11/2023 Burnam
2024/0389870 A1 11/2024 Han

FOREIGN PATENT DOCUMENTS

CN 106037698 10/2016
CN 110099607 8/2019
CN 110301906 10/2019
CN 110301907 10/2019
GB 2575945 1/2020
JP 3120617 U 3/2006
JP 3121082 U 4/2006
JP 2008178541 8/2008
JP 2020043931 3/2020
JP 2021143647 9/2021
KR 20180033018 4/2018
WO WO 11/023343 3/2011
WO WO 19/010615 1/2019
WO WO 20/016139 1/2020
WO WO 20/039826 2/2020

OTHER PUBLICATIONS

U.S. Appl. No. 17/398,775, filed Aug. 10, 2021, Jain et al.
Horsey, "YHE smartwatch wearable blood pressure monitor," geeky-gadgets.com/wearable-blood-pressure-monitor-07-02-2020, Feb. 7, 2020, 3 pages.
U.S. Appl. No. 16/928,933, filed Jul. 14, 2020, Lee et al.
U.S. Appl. No. 16/998,902, filed Aug. 20, 2020, Tadele et al.
U.S. Appl. No. 17/166,914, filed Feb. 3, 2021, Han et al.
U.S. Appl. No. 17/899,443, filed Aug. 30, 2022, Smith et al.

(56) References Cited

OTHER PUBLICATIONS

U.S. Appl. No. 17/900,678, filed Aug. 31, 2022, Tadele et al.

* cited by examiner

STRETCHABLE BLOOD PRESSURE CUFF

CROSS-REFERENCE TO RELATED APPLICATION

This application is a nonprovisional of, and claims the benefit under of 35 U.S.C. § 119(e) of, U.S. Provisional Patent Application No. 63/011,061, filed Apr. 16, 2020, the contents of which are incorporated herein by reference as if fully disclosed herein.

FIELD

The described embodiments relate generally to methods, devices and systems for measuring physiological parameters of a user. More particularly, the present embodiments relate to cuffs that can be worn around a limb of a user to secure a blood pressure measurement device to the user.

BACKGROUND

A user may monitor one or more of their physiological parameters by attaching a monitoring device such as a blood pressure monitor to one of their limbs. The blood pressure monitor may include an inextensible cuff that secures an inflatable bladder against a limb of the user. The inflatable bladder can be expanded, and the inextensible cuff may cause the bladder to compress the limb, thereby compressing one or more blood vessels in the limb and restricting and/or stopping blood flow through the vessels. The various pressures in the inflatable bladder that restrict and/or stop blood flow through the vessels in the limb may be measured and used to determine one or more physiological parameters of a user such as blood pressure of the user.

A physiological monitoring device such as blood pressure cuff is typically worn during the measurement, and is removed promptly thereafter. In some cases, it might be desirable to wear the monitoring device for longer periods of time such that physiological measurements can be performed at periodically or continuously.

SUMMARY

Embodiments include devices and techniques for performing blood pressure measurements that include a cuff that can transition between a stretchable state to accommodate movement of a user while the cuff is being worn and a locked state where the cuff becomes inextensible while taking a blood pressure measurement.

In a first aspect, the present disclosure is directed to a cuff for measuring blood pressure of a user. The cuff can include a bladder assembly configured to retain a fluid within an internal chamber. The bladder assembly can include a first cell defining a first portion of the internal chamber and a second cell in fluid communication with the first cell and defining a second portion of the internal chamber. The bladder assembly can also include a fluid passage in fluid communication with the first cell and the second cell. The cuff can further include a reservoir coupled with the fluid passage and configured to exchange the fluid with the bladder assembly. The bladder assembly can be configured to increase in length when a volume of the fluid in the internal chamber decreases and decrease in length when the volume of the fluid in the internal chamber increases.

In some embodiments, the cuff can also include a valve positioned between the bladder assembly and the reservoir. The bladder assembly can include a top sheet and a bottom sheet joined with the top sheet, where the first cell is a first elongated tube, the second cell is a second elongated tube and the first elongated tube and second elongated tube are both formed by coupling sections of the top sheet to the bottom sheet. The fluid passage can be defined by the top and bottom sheets and the valve can be configured to control the exchange of the fluid between the bladder assembly and the reservoir.

In some embodiments the cuff can include a valve positioned between the bladder assembly to the reservoir; where the valve is configured to switch between a first state in which the fluid can move between the bladder assembly and the reservoir, and a second state that prevents the fluid from moving between the bladder assembly and the reservoir. In some cases, the cuff can include a housing coupled to the bladder assembly, where the reservoir and the valve are located within the housing. The reservoir can include an elastic member that is configured to increase a pressure of the fluid as the volume of the fluid in the reservoir increases. In some examples, the first cell defines a first elongated tube, the second cell defines a second elongated tube and the first and second elongated tubes are configured to extend along a length of a limb of the user when the cuff is worn by the user. In some embodiments, the bladder assembly can include a top sheet and a bottom sheet joined to the top sheet to define the first cell, the second cell and the fluid passage. The bottom sheet may be joined to the top sheet at defined locations such that the top sheet and the bottom sheet are substantially inseparable at the defined locations. The defined locations may form fluid impermeable barriers within the internal chamber.

In another aspect, the present disclosure is directed to a wearable cuff that includes a bladder assembly configured to contain a fluid. The bladder assembly may be defined by an outer component that is liquid impermeable and defines a series of expandable channels and an inner component and formed from a fluid permeable material that has a lower compliance than the outer component. The wearable cuff can also include a reservoir coupled with the bladder assembly and configured to exchange the fluid with the bladder assembly. The bladder assembly can be configured to increase in length when a volume of the fluid within the bladder assembly decreases and decrease in length when the volume of the fluid within the bladder assembly increases.

In some embodiments, the outer component is formed from a first sheet joined with a second sheet and the inner component is positioned between the first sheet and the second sheet. The inner component can be configured to bias the bladder assembly toward a contracted state in which the length of the bladder assembly is decreased. The inner component can be formed from an elastic material that is coupled to the outer component. In some examples, the outer component defines first and second edges and includes relief features extending along the first and second edges. The relief features can be defined by a series of recesses formed along the first and second edges of the outer component. The relief features may increase a range of motion of the bladder assembly.

In another aspect, the present disclosure is directed to a wearable blood pressure measuring device that includes a cuff defining an interior surface that at least partially wraps around a user's limb and a first bladder assembly coupled with the cuff and defining a chamber. The first bladder assembly can be configured to contain a fluid and maintain a constant circumferential dimension when a volume of the fluid within the chamber is held constant. The wearable blood pressure measuring device can also include a reservoir configured to exchange the fluid with the first bladder assembly, a valve configured to control the exchange of the fluid between the first bladder assembly and the reservoir and a second bladder assembly positioned along a portion of the interior surface and configured to expand and contract when the user's blood pressure is measured. The valve can be configured to prevent movement of fluid between the first bladder assembly and the reservoir in response to measuring the user's blood pressure, which can result in the volume of the fluid within the chamber, is held constant in response to measuring the user's blood pressure.

In some embodiments, the valve allows movement of fluid between the first bladder assembly and the reservoir when the user's blood pressure is not being measured. The circumferential dimension of the first bladder assembly may be further configured to expand and contract when the valve allows movement of fluid between the first bladder assembly and the reservoir. In some examples, the cuff is formed from a substantially inextensible material.

BRIEF DESCRIPTION OF THE DRAWINGS

The disclosure will be readily understood by the following detailed description in conjunction with the accompanying drawings, wherein like reference numerals designate like structural elements, and in which.

Figure 1:
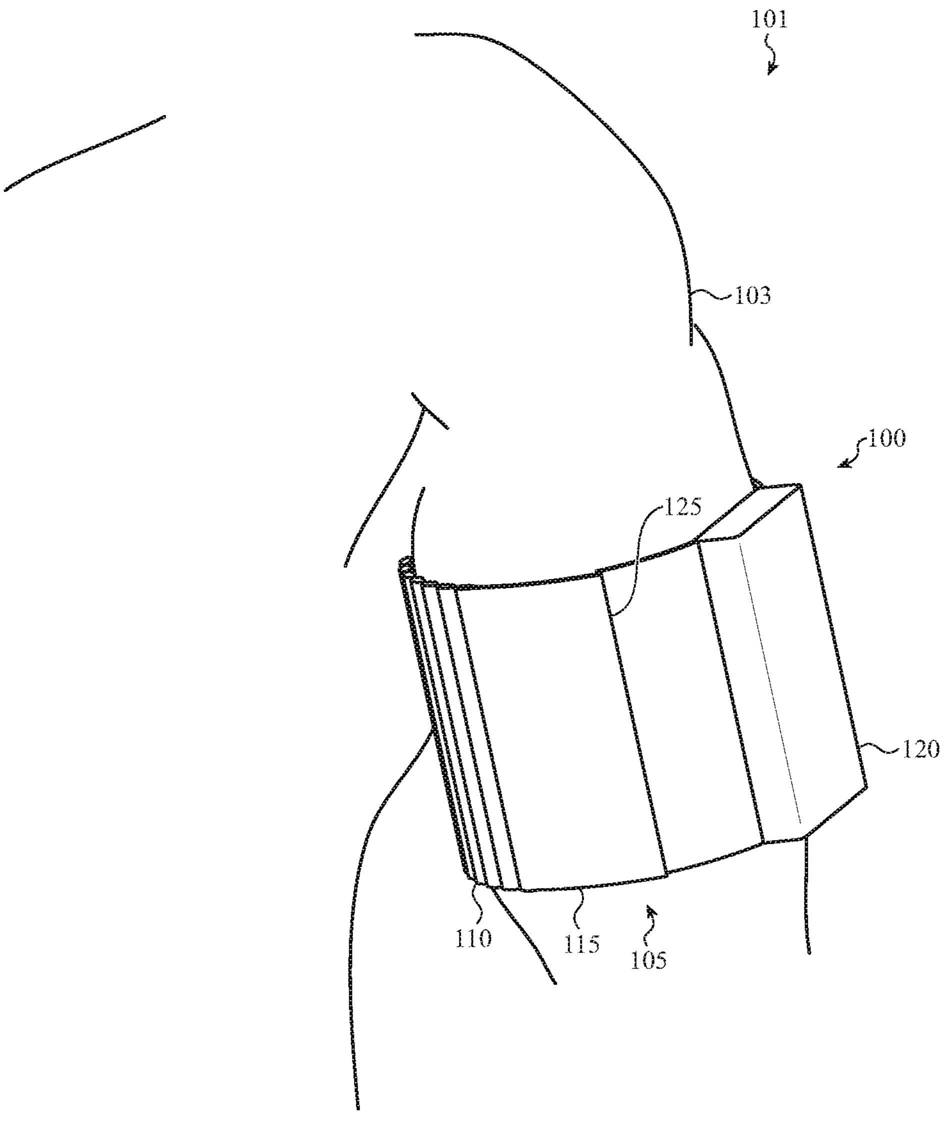
FIG. 1 illustrates an example of a blood pressure measurement device as worn by a user.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates to devices and techniques for a blood pressure measurement device that includes a cuff that can transition between a stretchable state to accommodate movement of a user while the cuff is being worn and a locked state where the cuff becomes inextensible while taking a blood pressure measurement. The blood pressure cuff may include a measurement bladder that is inflated, such that it expands against a user's limb to restrict and/or stop blood flow through vessels in the user's limb. The blood pressure measurement device may include one or more sensors that measure various pressures in the measurement bladder and determine the pressures that restrict and/or stop blood flow through the user's vessels, which may be used to determine a blood pressure of the user.

When taking a blood pressure measurement, it may be desirable to have a cuff that is substantially inextensible, such that it maintains a constant circumferential dimension when the measurement bladder is inflated. For example, if the cuff remains relatively inextensible when the measurement bladder inflates, the cuff can cause the measurement bladder to primarily expand toward the user's limb, thereby compressing the tissue and blood vessels in the user's limb instead of causing the cuff to expand. In some cases, an inextensible cuff may result in more accurate blood pressure measurements due to the lower amount of expansion required to compress a user's arm and/or result in more efficient operation of the physiological measurement device due to less work required by the hardware components (such as a compressor or air pump).

In some embodiments, the cuff can include a first section that can transition between the stretchable state and the locked state, a second section that is relatively inextensible and a measurement bladder that is at least partially located along an interior of the cuff. The cuff may be worn around a limb of a user and be operated in the stretchable state when it is not being used to take a blood pressure measurement of the user. Accordingly, in the stretchable state, the cuff may expand and contract to accommodate changes in the size of the user's limb as the user performs various movements (flexes). The cuff may be operated in the locked state while taking a blood pressure measurement of a user. In the locked state, the first section may become essentially inextensible, such that the cuff maintains a constant circumferential dimension while the measurement bladder is expanded to perform the blood pressure measurement.

The first section can include an expandable bladder assembly that contains a fluid and is coupled with a reservoir, such that the fluid can move between the expandable bladder assembly and the reservoir. In some cases, the expandable bladder is in addition to and distinct from the measurement bladder. For example, the first section of the cuff formed by the expandable bladder may be a distinct section that defines both interior and exterior surfaces of the first portion of the cuff. The second (inextensible) portion of the cuff can include a second distinct section, where the first and second sections are joined to wrap around a limb of a user. In some cases, the cuff can include a fastening mechanism that joins different ends of the cuff together to form a continuous structure around a user's limb. The measurement bladder can be positioned along an interior portion of the cuff when the cuff is worn by a user.

In some embodiments, the cuff also contains a valve that can be positioned between the expandable bladder assembly and the reservoir. The valve may operate as a locking mechanism to transition the cuff between the stretchable state and the locked state by either allowing or stopping the movement of fluid between the bladder assembly and the reservoir. For example, the bladder assembly may be configured to increase in length when fluid contained within the bladder assembly moves into the reservoir (where a volume of fluid in the bladder assembly decreases), and decrease in length when fluid moves from the reservoir and into the bladder assembly (where a volume of fluid in the bladder assembly increases). As such, in the stretchable state, the valve may be opened to allow fluid to move between the bladder assembly and the reservoir, thereby allowing the first section of the cuff to expand and contract in length. In the locked state, the valve can be closed to prevent the movement of fluid between the bladder assembly and the reservoir, thereby maintaining the first section of the cuff at a constant length.

In some cases, the reservoir may be configured to apply a pressure on the fluid contained within the reservoir to bias fluid to move from the reservoir and into the expandable bladder assembly. For example, the reservoir may include an elastic material that increases in tension in response to fluid moving into the reservoir thereby increasing a pressure on the fluid as more fluid moves into the reservoir. Such a biasing mechanism may maintain contact between the cuff and a limb of the user, as the user moves around, by allowing fluid to flow into the reservoir when the user's limb expands the cuff and pushing fluid back to the bladder to decrease the size of the cuff when the user's limb contracts. In some examples, the expandable bladder can include an elastic component (for example, an elastic material) contained within the internal chamber and coupled with the bladder assembly. Such an elastic component may be configured to bias the bladder assembly toward a shortened length when the bladder assembly is in a stretchable state to maintain contact between the cuff and a user's limb when the user is moving.

These and other embodiments are discussed below with reference to FIGS. 1-11. However, those skilled in the art will readily appreciate that the detailed description given herein with respect to these Figures is for explanatory purposes only and should not be construed as limiting.

FIG. 1 illustrates an example of a blood pressure measurement device 100 as worn by a user 101. The blood pressure measurement device 100 can include a cuff 105 that wraps around a limb 103 of a user 101. The cuff 105 can include a first section 110 that transitions between a stretchable state and a locked state and a second section 115 that is relatively inextensible. The first section 110 and the second section 115 can wrap around a limb 103 of a user 101 such that the cuff 105 encircles the limb 103. The blood pressure measurement device 100 can also include a housing 120 that is coupled to the cuff 105.

In some embodiments, the first section 110 is coupled to the second section 115 such that the cuff 105 defines an elongated sheet that extends from a first end to a second end. The cuff 105 can be wrapped around the limb 103 and the first and second ends can be coupled by a fastening mechanism 125. In some examples, the fastening mechanism 125 can include any suitable mechanism that secures the first and second ends of the cuff 105 together while the cuff 105 is being worn by the user 101. Examples of fastening mechanisms 125 can include hook-and-loop fasteners, clips, zippers, buttons, and so on. In some examples, the first and second ends of the cuff 105 can be permanently joined and the cuff 105 can be placed on the limb 103 by a user 101 sliding their limb 103 through a central opening define by the cuff 205.

The housing 120 can include components that are used to take a blood pressure measurement. In some embodiments, the housing 120 can include an air pump for inflating a measurement bladder (not shown) that is positioned along at least a portion of the interior of the cuff 105. The housing 120 can further include one or more components for operating a pressure sensor that is used to measure a pressure within the measurement bladder and/or detect changes in pressure due to blood flow through the user's 101 vessels when the cuff 105 is wrapped around the user's 101 limb 103. In some embodiments, the housing 120 can also include components for operating an auditory sensor that is used to detect changes in the blood flow through vessels in the limb 103. For example, the auditory sensor may be configured to detect a change in sound of the blood flow through vessels due to the vessels being restricted (partially compressed) due to expansion of the measurement bladder. The auditory sensor may also be configured to detect a change in sound of the blood flow through the vessels due to the vessels being closed (completely compressed) due to further expansion of the measurement bladder. The housing 120 can also include one or more other components such as a processor, memory, a battery, and so on that are used to perform blood pressure measurement of the user 101.

The cuff 105 may be operated in the stretchable state when it is not being used to perform a blood pressure measurement of the user 101. In the stretchable state, the first section 110 may expand and contract to accommodate changes in the size of the limb 103, for example, due to the user 101 moving/flexing their limb 103. In this state, the first section 110 may respond to user movements in an elastic-like manner. For example, a user 101 may flex their limb 103 causing it to expand, and the first section 110 can lengthen/extend in a circumferential direction thereby increasing the circumferential length of the cuff 105 to accommodate the expansion of the limb 103. A user 101 may also relax their limb 103 causing it to decrease in size, and the first section 110 can shorten/contract in length thereby decreasing the circumferential length of the cuff 105 and maintaining contact with the limb 103 as it decreases in size. The first section 110 may be configured to secure the cuff 105 (and housing 120) to the limb 103 such that the blood pressure measurement device 100 remains in place on the limb 103 during normal movements performed by the user 101. In the stretchable state, the first section 110 may cause the cuff to contract around the limb 103 to secure the cuff 105 to the limb 103, while still allowing the limb 103 to expand and contract without stopping or substantially restricting blood flow through the limb 103.

The cuff 105 may also be operated in the locked state while taking a blood pressure measurement of a user 101. In the locked state, the first section 110 may become essentially inextensible and the second section 115 may be permanently inextensible such that the cuff 105 maintains a constant circumferential length while the measurement bladder is expanded to perform the blood pressure measurement. In the locked state, the first section 110 may be operated such that it does not increase in length in response to changes in the size of the limb 103. As used herein, the term inextensible or substantially inextensible means that the component does not lengthen a substantial amount under the forces/pressures experienced by the cuff 105 when a blood pressure measurement is being taken.

Figure 2:
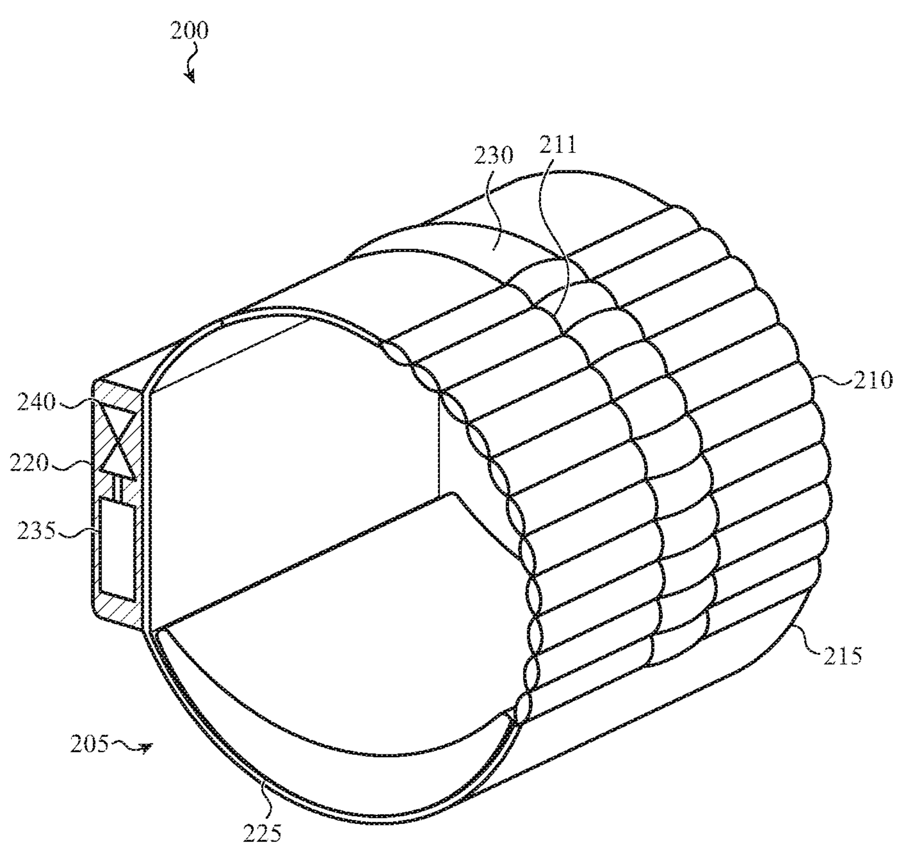
FIG. 2 illustrates an example of a blood pressure measurement device.

FIG. 2 illustrates an example of a blood pressure measurement device 200 in a closed configuration as it would be worn by a user. The blood pressure measurement device 200 can include a cuff 205 having a bladder assembly 210 and a second section 215, which may be an example of the cuffs described herein (such as cuff 105 having first section 110 and second section 115); a housing 220, which may be an example of the housing 120; and a measurement bladder 225, which may be an example of the measurement bladders described herein. The blood pressure measurement device can also include a fluid passage 230, a reservoir 235 and a valve 240.

In some embodiments, the first section can include an expandable bladder assembly 210 that can be operated to transition between the stretchable state and the locked state. The bladder assembly 210 defines an internal chamber 211 that is configured to contain a fluid. The cuff 205 may also include a fluid passage 230 that extends between the bladder assembly 210 and the reservoir 235, which may also be configured to contain the fluid. The fluid passage 230 couples the bladder assembly 210 to the reservoir 235, such that fluid can move between the bladder assembly 210 and the reservoir. In some embodiments, the combined fluid volume in the bladder assembly 210, the fluid passage 230 and the reservoir may be constant. Accordingly, the volume of fluid in the bladder assembly 210 and the reservoir 235 may be inversely related as fluid moves between these two components. For example, fluid can move from the bladder assembly 210, through the fluid passage 230 and to the reservoir 235 thereby decreasing the fluid volume in the bladder assembly 210 and increasing the fluid volume in the reservoir 235.

The bladder assembly 210 may include a length that extends around at least a portion of the circumference of the cuff 205 and a thickness that extends from an interior of the cuff 205 to an exterior of the cuff (transverse to the length). The bladder assembly 210 can be configured, such that when it is empty (or nearly empty), the internal chamber 211 is collapsed and the length of the bladder assembly 210 is in an elongated state. As the bladder assembly is filled with fluid from the reservoir 235, the volume of the internal chamber 211 increases thereby increasing the thickness and causing the length of the bladder assembly 210 to shorten. In some cases, the bladder assembly 210 may be formed from a first sheet and a second sheet that are coupled together at defined locations to form the interior chamber. The portions where the first and second sheets are coupled may form sections of the bladder that are impermeable to fluid and the portions of the first and second sheets that are not coupled may separate/move relative to each other to define the internal chamber 211.

In some embodiments, a valve 240 can be positioned between the bladder assembly 210 and the reservoir 235. The valve 240 can be configured to control the movement of fluid between the bladder assembly 210 and the reservoir 235, which can be used to switch the bladder assembly between the stretchable state and the locked state. To operate the bladder assembly 210 in the stretchable state the valve 240 can be opened to allow fluid to move between the bladder assembly 210 and the reservoir 235. Accordingly, as the user's limb expands, fluid can be moved from the bladder assembly 210 and into the reservoir thereby collapsing the internal chamber 211 and increasing a length of the bladder assembly 210. Also, in the stretchable state, the bladder assembly 210 can decrease in length in response to a decrease in size of a user's limb such as due to relaxing of a flexed muscle. For example, as the size of the limb decreases, fluid can be moved from the reservoir 235 and into the bladder assembly 210 thereby expanding the internal chamber 211 and decreasing the length of the bladder assembly 210.

The bladder assembly may be operated in a locked state by closing the valve 240 to prevent the movement of fluid between the bladder assembly 210 and the reservoir 235. In the locked state, because fluid cannot move into or out of the bladder assembly 210 and the volume of fluid in the internal chamber 211 remains constant. The constant volume of fluid in the internal chamber 211 can maintain the bladder assembly at a substantially constant length. While the bladder assembly 210 is being operated in the locked state, the measurement bladder 225 can be inflated to take a blood pressure measurement of a user. The locked state of the bladder assembly 210 may make the cuff 205 inextensible such that during the blood pressure measurement, the measurement bladder 225 primarily expands towards and compresses the limb of the user.

Figure 3A:
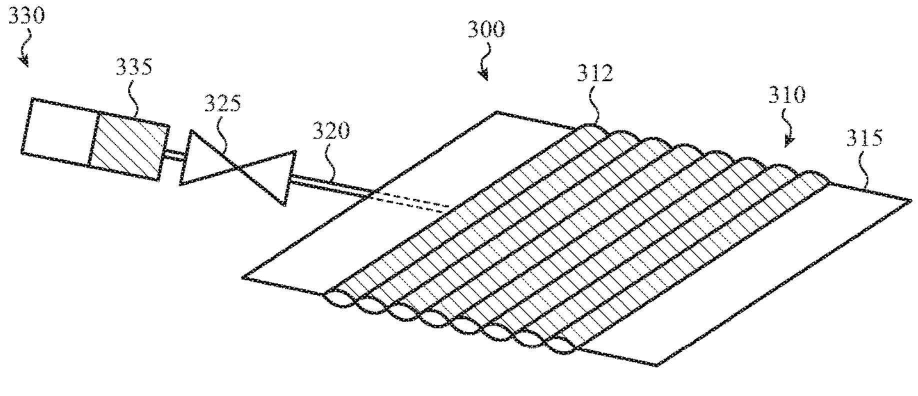
FIGS. 3A-3D illustrate example operations of a cuff including an expandable bladder assembly.
Figure 3B:
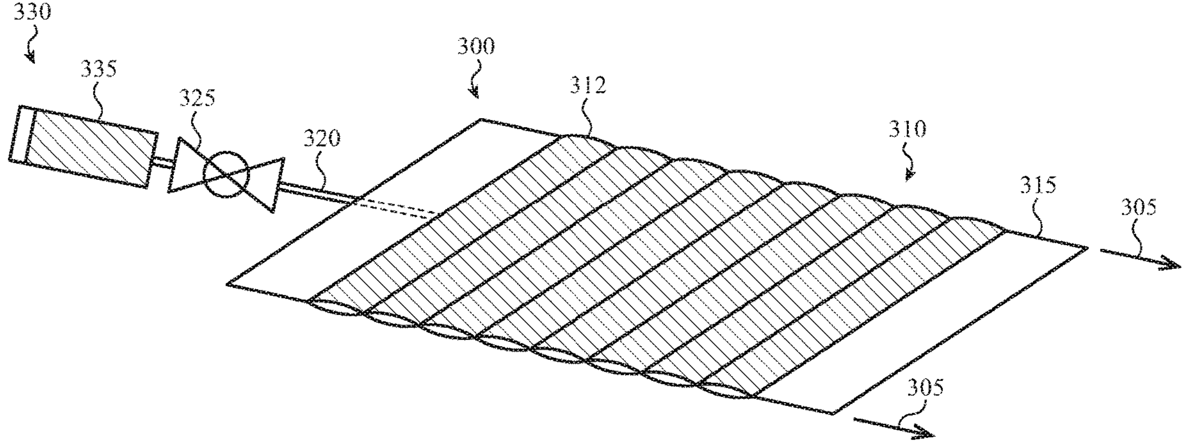
Figure 3C:
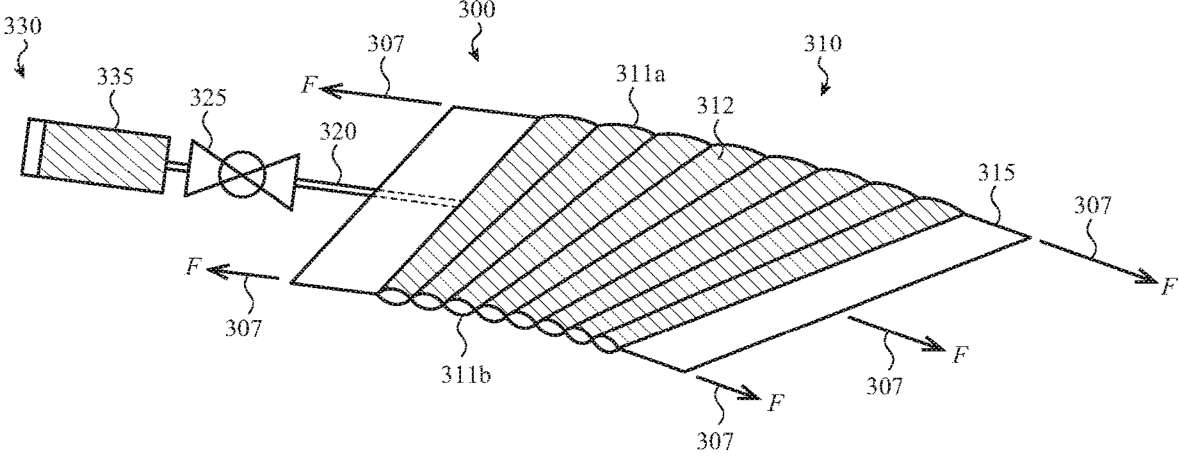

FIGS. 3A-3C illustrate an example operation of a cuff 300 including an expandable bladder assembly 310. The cuff 300 may be an example of the cuffs described herein, such as cuffs 105 and 205; and the bladder assembly 310 may be an example of the bladder assemblies described here, such as bladder assembly 210. The bladder assembly 310 is coupled to a reservoir 330 via fluid passage 320 and valve 325, which may be examples of the reservoir, fluid passage and valves described herein, such as reservoir 235, fluid passage 230 and valve 240. The bladder assembly 310 can include cells 312 that each defines a portion of an internal chamber of the bladder assembly 310.

FIG. 3A illustrates an example of the bladder assembly 310 in an initial state. As described herein, the bladder assembly 310 and the reservoir 330 may contain a fluid 335 that can move between the bladder assembly 310 and the reservoir 330. In the initial state, the bladder assembly 310 may contain a first volume of the fluid 335 and the reservoir may contain a second volume of fluid 335. The fluid 335 in the bladder assembly 310 may be distributed between the cells 312, such that the cells 312 are in an at least partially expanded state. In some embodiments, the cells 312 each form an elongated tube that are fluidly connected to each other, such that the fluid 335 can flow between the cells.

FIG. 3B illustrates operation of the cuff 300 in the stretchable state in response to an applied force 305 such as due to expansion of a user's limb. In the stretchable state, the valve 325 is open thereby allowing the exchange of fluid 335 between the bladder assembly 310 and the reservoir 330. As the force 305 is applied to the cuff 300, pressure is exerted by the bladder assembly 310 (cells 312) on the fluid 335 contained within the bladder assembly 310, which causes the fluid 335 to move from the bladder assembly 310 and into the reservoir 330 (via fluid passage 320 and valve 325). As a result of the fluid moving out of the bladder assembly 310, the cells 312 can collapse thereby increasing the length of the bladder assembly 310 in response to the applied force 305.

FIG. 3C illustrates the cuff 300 in a non-uniform stretchable state, which may occur in response to a non-uniform force 307 being exerted on the cuff 300 (for example, due to non-uniform expansion of a user's limb). In the example of FIG. 3C, the cuff is in the stretchable state and the valve 325 is open to allow the exchange of fluid between the bladder assembly 310 and the reservoir 330. As the non-uniform force 307 is applied to the cuff 300, a first edge 311*a* of the bladder assembly 310 may experience a greater force and a second edge 311*b* of the bladder assembly 310 may experience a lesser force, for example, due to the aforementioned non-uniform expansion of a user's limb. The portion of the cells 312 along the first edge 311*a* can expand a greater amount as compared the portions of the cells 12 along the second edge 311*b*, thereby conforming to the non-uniformly expanded limb. The fluid 335 contained within the bladder assembly 310 can shift within the cells 312 and/or move between the reservoir 330 and the cells 312 to accommodate the non-uniform movement of the cuff 300. Accordingly, the cuff may deform non-uniformly to maintain contact and conform to a user's limb as they perform various movements that change the shape of the limb.

Figure 3D:
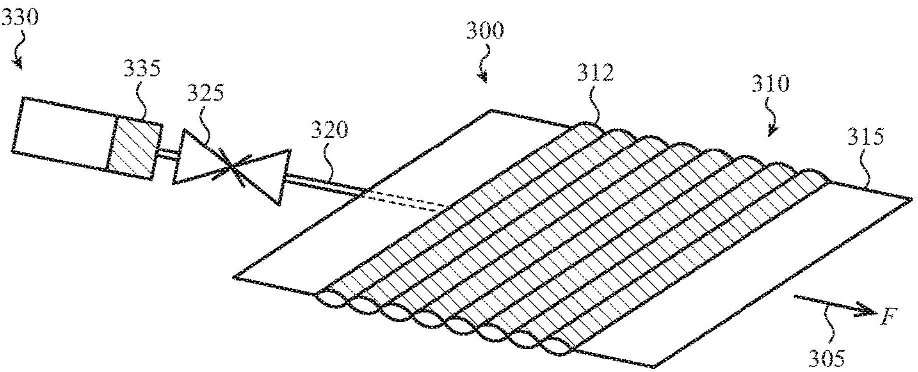

FIG. 3D illustrates operation of the cuff 300 in the locked state in response to an applied force 305 such as due to expansion of the measurement bladder as described herein. In the locked state, the valve 325 is closed thereby preventing the exchange of fluid 335 between the bladder assembly 310 and the reservoir 330. Accordingly, as the force 305 is applied to the cuff 300, pressure is exerted by the bladder assembly 310 (cells 312) on the fluid 335 contained within the bladder assembly 310, but the closed valve 325 prevents this fluid 335 from moving into the reservoir 330. As a result, the cells 312 do not collapse and the length of the bladder assembly 310 remains constant.

Figure 4A:
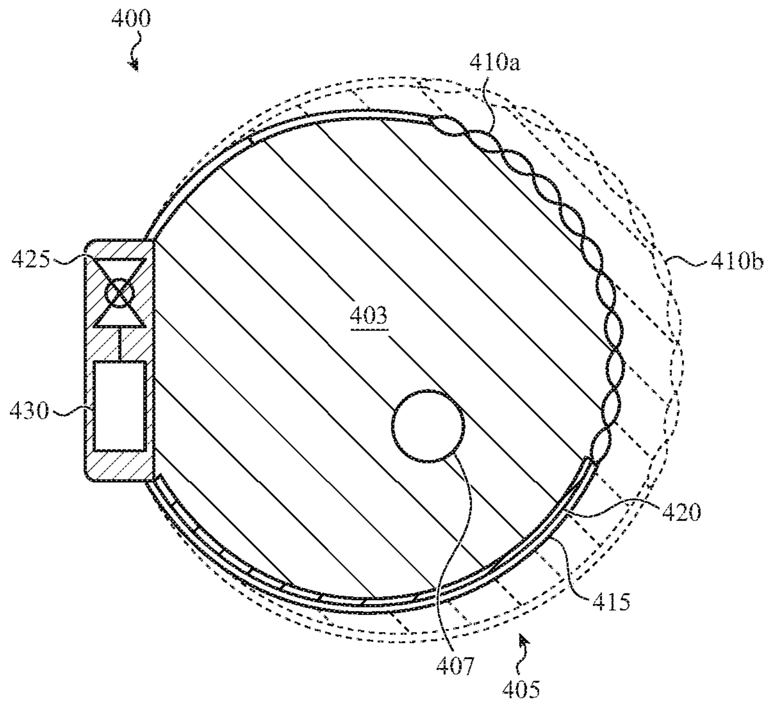
FIGS. 4A and 4B illustrate an example of operation of a blood pressure measurement device.
Figure 4B:
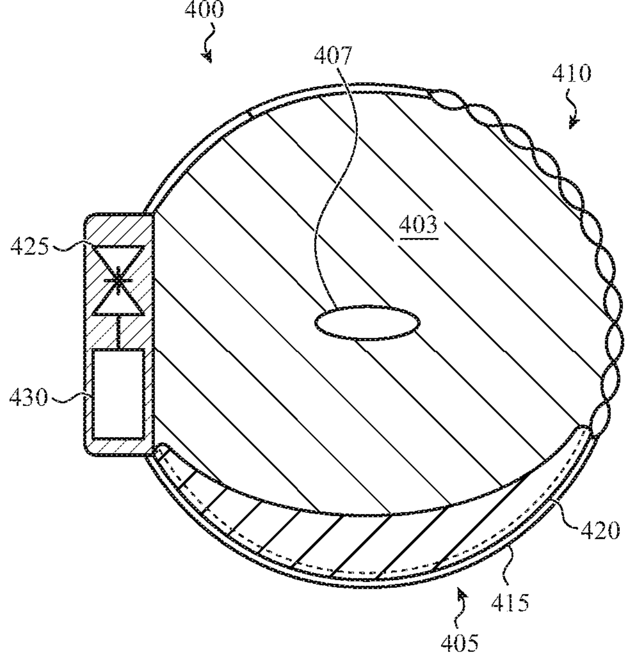

FIG. 4A-4B illustrate an example operation of a blood pressure measurement device 400. The blood pressure measurement device 400 can include a cuff 405, which may be an example of the cuffs described herein such as cuffs 105, 205 and 300; a bladder assembly 410, which may be an example of the bladder assemblies described herein such as bladder assemblies 210 and 310; a second section 415, which may be an example of the second section described herein, such as second section 115; measurement bladder 420, which may be an example of the measurement bladders described herein such as measurement bladder 225; valve 425, which may be an example of the valves described herein such as valves 240 and 325; and reservoir 430, which may be an example of the reservoirs described herein, such as reservoirs 235 and 330.

In the examples of FIGS. 4A and 4B, the blood pressure measurement device 400 is being worn around a limb 403 of a user. FIG. 4A illustrates operation of the blood pressure measurement device 400 when the bladder assembly is operated in a stretchable state. As described herein, in the stretchable state, the valve 425 may be open thereby allowing fluid to move between the bladder assembly 410 and the reservoir 430. The bladder assembly 410*a* is an initial contracted state that maintains contact with the limb 403, while applying pressure to the limb 403 that does not collapse the blood vessels in the limb such as blood vessel 407. In this initial state, the bladder assembly 410*a* has a shortened length and the cuff 405 has a first circumferential length. As the user's limb 403 expands, the bladder assembly 410*b* may increase in length to an expanded state to accommodate the increase in the size of the limb 403. In this second state, the bladder assembly 410*b* has an expanded length thereby increasing the circumferential length of the cuff 405. In the stretchable state, the measurement bladder 420 may remain deflated.

FIG. 4B illustrates operation of the blood pressure measurement device 400 when the bladder assembly 410 is operated in the locked state. As described herein, in the locked state, the valve 425 may be closed thereby preventing fluid from moving between the bladder assembly 410 and the reservoir 430. While, the bladder assembly is locked, the measurement bladder 420 can be inflated and the circumferential dimension of the cuff 405 remains substantially constant. For example, any expansion of the cuff 405, such as due to elastic deformation of the cuff material, is small compared to the expansion of the measurement bladder 420. Accordingly, inflation of the measurement bladder 420 causes the limb 403 to compress, which compresses blood vessels, such as blood vessel 407, in the limb 403. The inflation and deflation of the measurement bladder 420 may be controlled to increase the pressure in the measurement bladder 420 to restrict (decrease the cross section) and/or stop blood flow through the blood vessel 407.

Figure 5A:
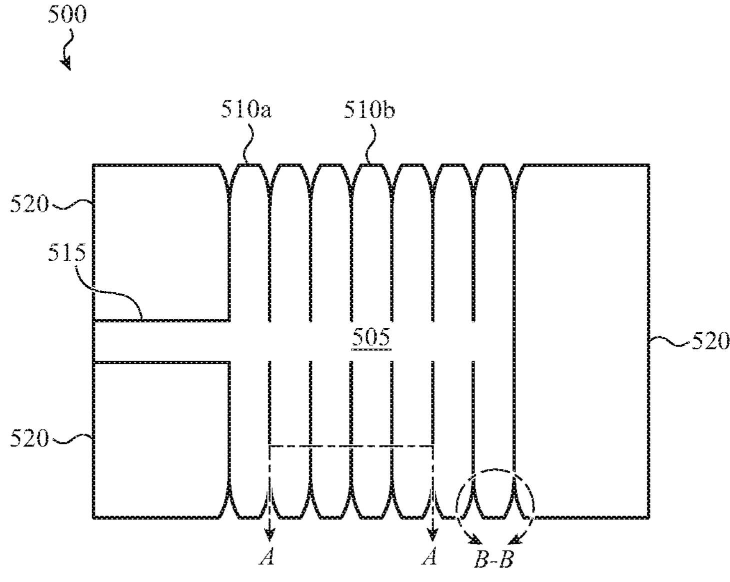
FIGS. 5A and 5B illustrate top and section views, respectively, of an example bladder assembly for use in a blood pressure measurement device.
Figure 5B:
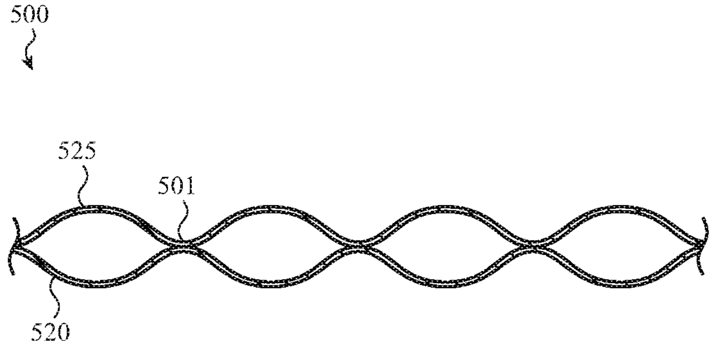

FIGS. 5A and 5B illustrate a top view and a section view taken along line A-A, respectively, of a bladder assembly 500 for use in a blood pressure measurement device. The bladder assembly 500 may be an example of the bladder assemblies described herein, such as bladder assemblies 210, 310 and 410. The bladder assembly 500 can include an internal chamber 505 that is configured to contain a fluid, and the internal chamber 505 may be defined by cells 510 which extend across a width of the bladder assembly 500. The bladder assembly 500 may also include a fluid passage 515 that extends between the cells 510 of the bladder assembly. As illustrated in FIG. 5B, the bladder assembly 500 may be formed by coupling a first sheet 520 to a second sheet 525 at defined locations 501. The locations 501 where the first and second sheets 520, 525 are coupled together may form a fluid impermeable barrier that defines the internal chamber 505.

In some embodiments, the first and second sheets 520, 525 may be formed from a fluid impermeable material such as a polymer, silicone, rubber or any other suitable material. In some cases, the first and second sheets 520, 525 can be formed from a material that is substantially inextensible under the forces used to take the blood pressure measurement. Such a material may reduce undesirable expansion of the bladder assembly 500, when a blood pressure measurement is being performed. In some embodiments, the sheets 520, 525 may be bonded using welding, adhesives, molding, crimping, sewing, and so on.

In some embodiments, the first and second sheets 520, 525 can be bonded at locations that define the structure of the bladder assembly. For example, outer portions 530 of the bladder assembly 500 may be bonded to seal the internal chamber 505 such that it retains a fluid. Similarly, the cells 510 may be formed by bonding intermittent sections of the top and bottom sheets 520, 525. For example, the top and bottom sheets 520, 525 may be bonded such that a first cell 510*a* defines a first elongated tube and a second cell 510*b* defines a second elongated tube. In other embodiments, the bladder assembly 500, and portions thereof, such as the internal cavity can be formed from other processes such as molding (e.g., injection, extrusion, blow, etc.), machining, sintering, and so on.

Figure 6A:
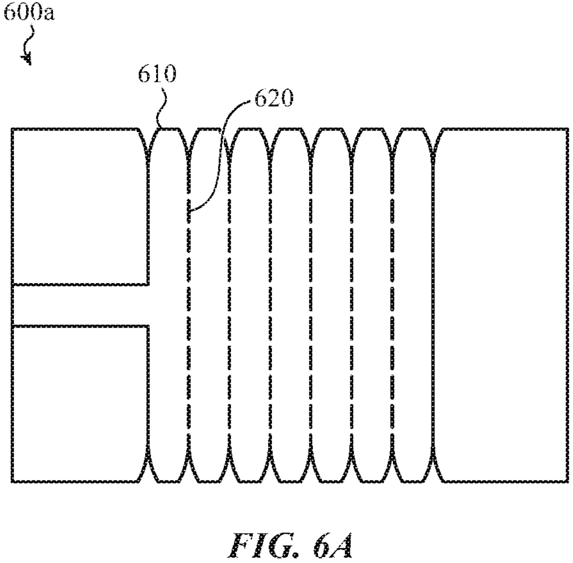
FIGS. 6A-6D illustrate examples of bladder assemblies for use in a blood pressure measurement device.

FIGS. 6A-6D illustrate examples of bladder assemblies 600 for use in a blood pressure measurement device. FIG. 6A illustrates an example of a bladder assembly 600*a* that includes cells 610 that are at least partially defined by a first pattern 620 of coupled and uncoupled sections of the top and bottom sheets as described herein. The first pattern 620 may create multiple openings between adjacent cells 610 (one of which is labeled), which may affect how fluid flows through the bladder assembly 600. For example, multiple larger openings defined by pattern 620 may increase the total cross-sectional area that is open for fluid to flow between adjacent cells 610, which can decrease the resistance of the fluid moving through the bladder assembly 600*a*, thereby increasing the rate of expansion and/contraction of the bladder assembly 600*a*.

Figure 6B:
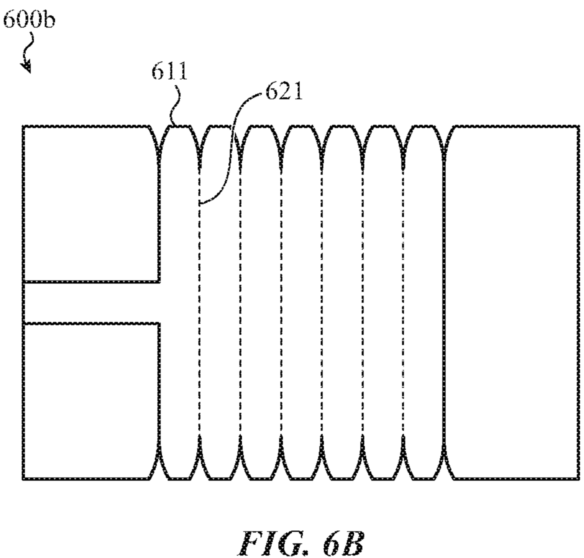

FIG. 6B illustrates an example of a bladder assembly 600*b* that includes cells 611 that are at least partially defined by a second pattern 621. The second pattern 621 may create multiple smaller openings between the adjacent cells 611, which may affect how fluid flows through the bladder assembly 600. For example, multiple smaller openings as defined by pattern 621 may increase the resistance of fluid moving through the bladder assembly 600*b*, thereby dampening or slowing the rate of expansion and/or contraction of the bladder assembly 600*b*.

Figure 6C:
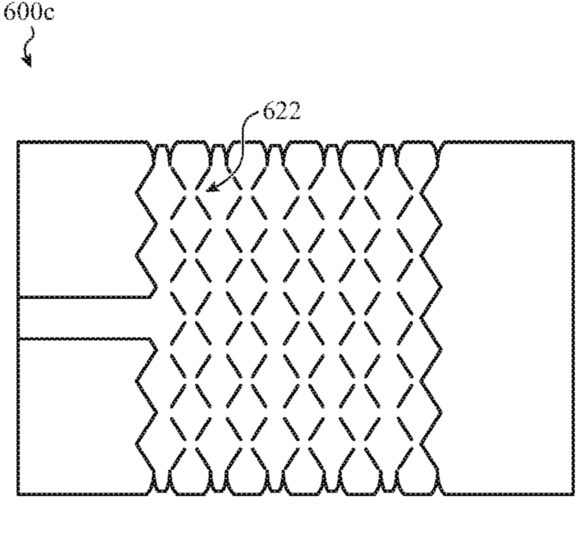
Figure 6D:
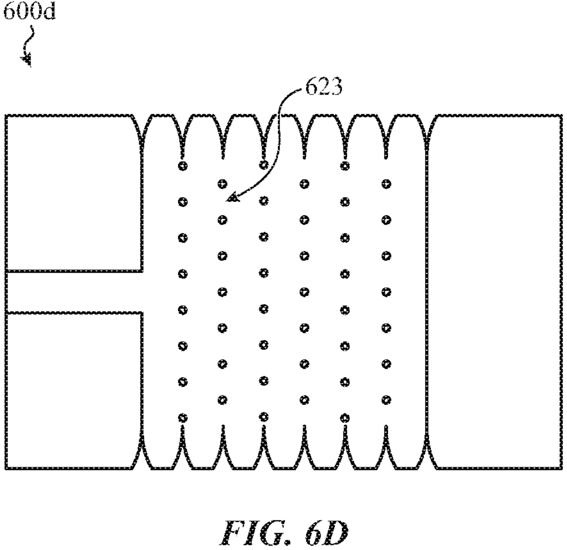

FIGS. 6C and 6D illustrate further examples of bladder assemblies 600*c* and 600*d*, respectively. FIGS. 6C and 6D, illustrate additional patterns 622 and 623 of coupled and uncoupled sections of the bladder assembly that may be used to define the internal chamber. The patterns 620, 621, 622 and 623 may also be used to define the exterior surface features of the bladder assembly 600. For example, some patterns may increase flexibility of the bladder assembly, increase comfort, help secure the cuff to the user, and so on. The illustrated patterns are provided as examples and are not intended to be limiting. Accordingly, one skilled in the art will realize that other patterns could be implemented.

Figure 7A:
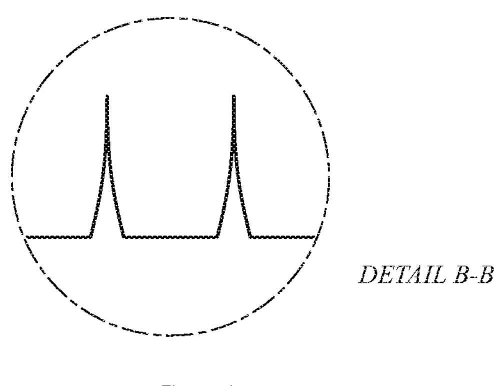
FIGS. 7A and 7B illustrate examples relief features that may be incorporated into bladder assemblies.
Figure 7B:
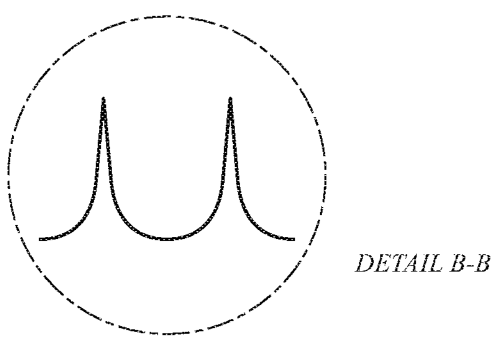

FIG. 7A shows detailed view B-B of a relief feature 700*a* from the bladder assembly 500 illustrated in FIG. 5A. FIG. 7B shows another example of a relief feature 700*b* that can be incorporated into the bladder assemblies described herein. The relief features 700 may be located on the edges of the bladder assembly and form separations between the ends of adjacent cells of the bladder assembly. The relief features may allow the ends of the cells to move relative to each other, which may help the cells more completely expand when the internal chamber is filled with fluid. In some cases, the relief features 700 may also increase the range of motion of the bladder assembly, which may help the cuff conform to a user's limb.

Figure 8A:
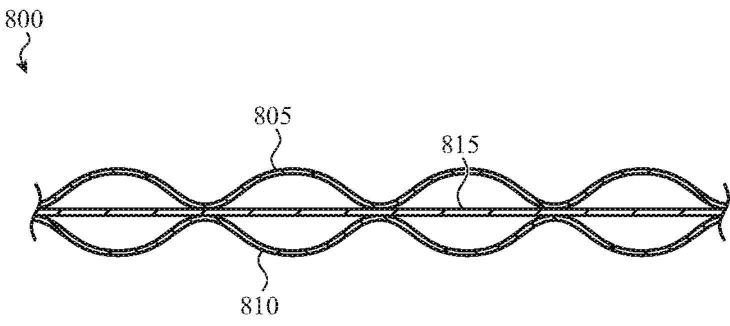
FIGS. 8A-8C illustrate cross-sectional views of examples of bladder assemblies for use in a blood pressure measurement device.
Figure 8B:
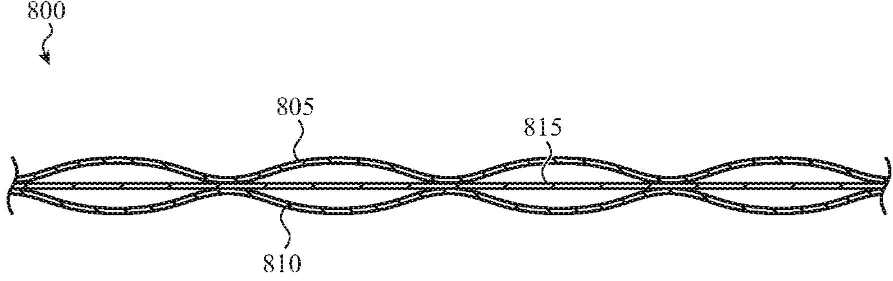

FIGS. 8A and 8B illustrate cross sectional views of an alternative embodiment of a bladder assembly 800 as taken along line A-A of FIG. 5A. The bladder assembly 800 may be an example of the bladder assembly described herein, such as bladder assemblies 210, 310, 410, 500 and 600. The bladder assembly 800 can include a first sheet 805, a second sheet 810 and elastic component 815 positioned between the first sheet 805 and the second sheet 810. As shown in FIG. 8A, the bladder assembly 800 may be in an initial, shortened configuration, in which the first and second sheets 805, 810 are expanded (separated) to define a cell within the internal chamber of the bladder assembly 800. The elastic component 815 can be coupled to the first and second sheets 805, 810 at the locations where these sheets join together as described herein. The elastic component may be in tension in the initial state, and bias the bladder assembly towards the shortened configuration. For example, the elastic component 815 may pull the joined sections of the first and second sheets 805, 810 closer together.

As shown in FIG. 8B, when the bladder assembly 800 is in an elongated state, the elastic component 815 is stretched and the distance between the first and second sheets 805, 806 decreases (cells become smaller). The stretching of the elastic component 815 may increase its tension to provide a larger biasing force on the bladder assembly to return to a shortened state. Accordingly, as the bladder assembly is stretched the elastic component 815, may increase its bias to return the bladder assembly toward a shortened state, which may help secure a cuff to a user when the cuff is operated in the stretchable mode.

In some cases, elastic component 815 may be made from a fluid permeable material such that fluid contained within the bladder assembly 800 can pass through the elastic component as it moves to and from the reservoir as described herein. The bias force produced by the elastic component 815 and the resistance of fluid movement through the bladder assembly 800, such as due to fluid resistance from the pattern of cells and/or the elastic component 815, can be used to obtain the desired pressure on the a user's limb.

Figure 8C:
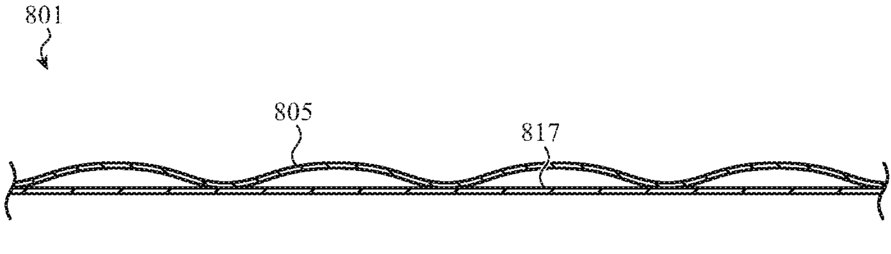

FIG. 8C illustrates a cross sectional view of another example embodiment of a bladder assembly 801 as taken along line A-A of FIG. 5A. The bladder assembly 801 may be an example of the bladder assembly described herein, such as bladder assemblies 210, 310, 410, 500 and 600. The bladder assembly 801 can include a first sheet 805 forming a first side of the bladder assembly 801 and elastic component 817 that is coupled with the first sheet 805 and forms a second side of the bladder assembly 801. The bladder assembly 801 can be configured such that the first sheet 805 and the elastic component 817 retain a fluid within an interior volume of the bladder assembly 801, as described herein. For example, the first sheet 805 and the elastic component can be formed from materials that are impermeable to fluids. As shown in FIG. 8C, the bladder assembly 801 may be in an initial, shortened configuration, in which the first sheet 805 and the elastic component 817 are separated to define cells within the internal chamber of the bladder assembly 801. The elastic component 817 and the first sheet 805 can be coupled at intermediate locations to define the cells as described herein.

In a first state, the elastic component may be in tension and in a shortened configuration, to bias the bladder assembly towards the shortened state. In the first (shortened) state, the tension of the elastic component 817 may cause the first sheet 805 to form a semicircular pattern such that the first sheet contacts the second sheet at the intermediate locations but is spaced apart from the second sheet between the intervals.

In a second state, the elastic component 817 elongates, for example in response to a force stretching the bladder assembly 801. As the bladder assembly 801 lengthens, the first sheet 805 moves toward the elastic component 817, thereby decreasing the volume of the cells. In the example of the FIG. 8C, the elastic component 817 may remain flat (while stretching) as the cuff transitions between the shortened and elongated configurations. The bladder assembly 801 may be configured such that the elastic component 815 contacts the limb of the user. The elastic component 817 remaining flat against the limb of the user throughout operation of the bladder assembly 801 may increase comfort of the cuff such as by reducing pressure points and/or pinch points on the user's arm. Additionally, lengthening the elastic component 817 as the bladder assembly lengthens can increase tension in the elastic component 817 and bias the bladder assembly toward the shortened state. Such biasing by the elastic component 817 can help conform the bladder assembly 801 to a user's arm and maintain contact between the bladder assembly 801 and the user's arm.

Figure 9A:
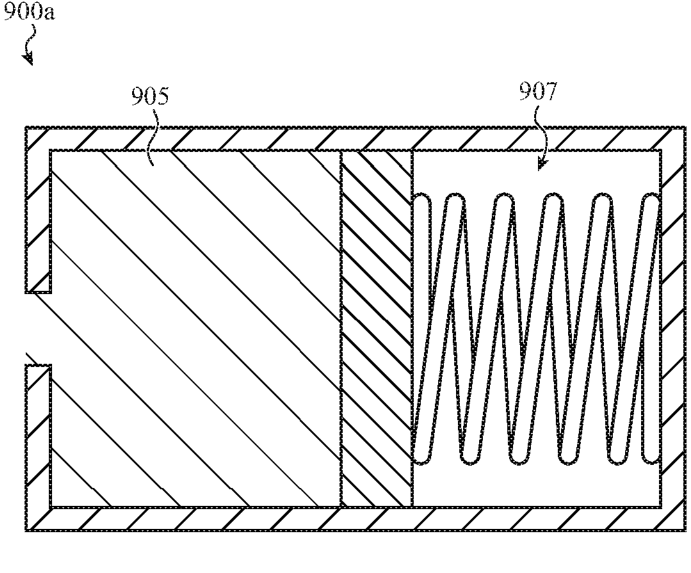
FIGS. 9A and 9B illustrates examples of reservoir components for use in a blood pressure measurement device.
Figure 9B:
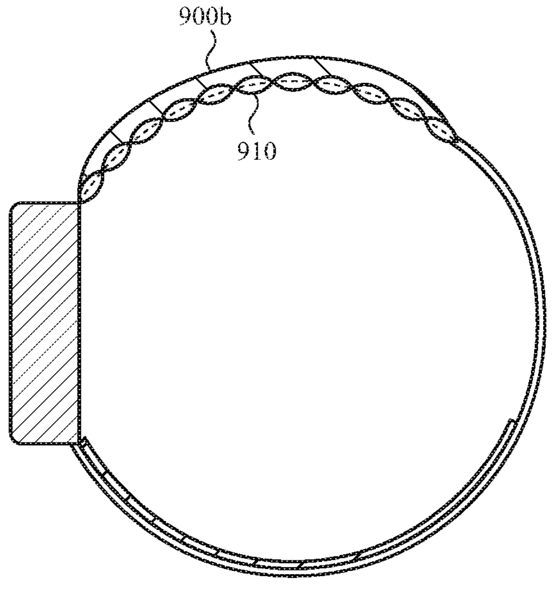

FIGS. 9A and 9B illustrates examples of reservoirs 900 for use in a blood pressure measurement device. The reservoirs 900 may be examples of the reservoirs described herein, such as reservoirs 235, 330 and 430. In the example of FIG. 9A, the reservoir 900*a* can include a fluid chamber 905 and a biasing member 907. The biasing member 907 can be configured to exert a pressure on the fluid in the chamber 905 and the bladder assembly (not shown). In some embodiments, the biasing member 907 can include an elastic element that is configured to increase a pressure exerted on the fluid as the volume of fluid in the fluid chamber 905 increases. In cases, where the valve between the bladder assembly and the reservoir 900 is open, and the fluid is able to move from the bladder assembly and into the reservoir 900*a*, the reservoir 900*a* may exert a pressure on the fluid thereby biasing the fluid to move into the bladder assembly. In some cases, the amount of pressure created by the biasing member 907 can be controlled to help secure the cuff to a user. For example, the biasing member 907 can apply a pressure on the fluid such that the bladder assembly remains in contact with the user's limb when the user moves and the limb expands or contracts.

FIG. 9B illustrates an example of a reservoir 900*b* that includes an elastic cavity 915 that retains fluid that is moved from the bladder assembly 910 and into the biasing member 907. As more fluid is moved into the elastic cavity 915, the cavity can expand and increase a pressure exerted on the fluid. The elastic cavity 915 can be positioned on the cuff, such as along the outer surface of the cuff. In some cases, the elastic cavity 915 can partially overlap the bladder assembly 910.

Figure 10:
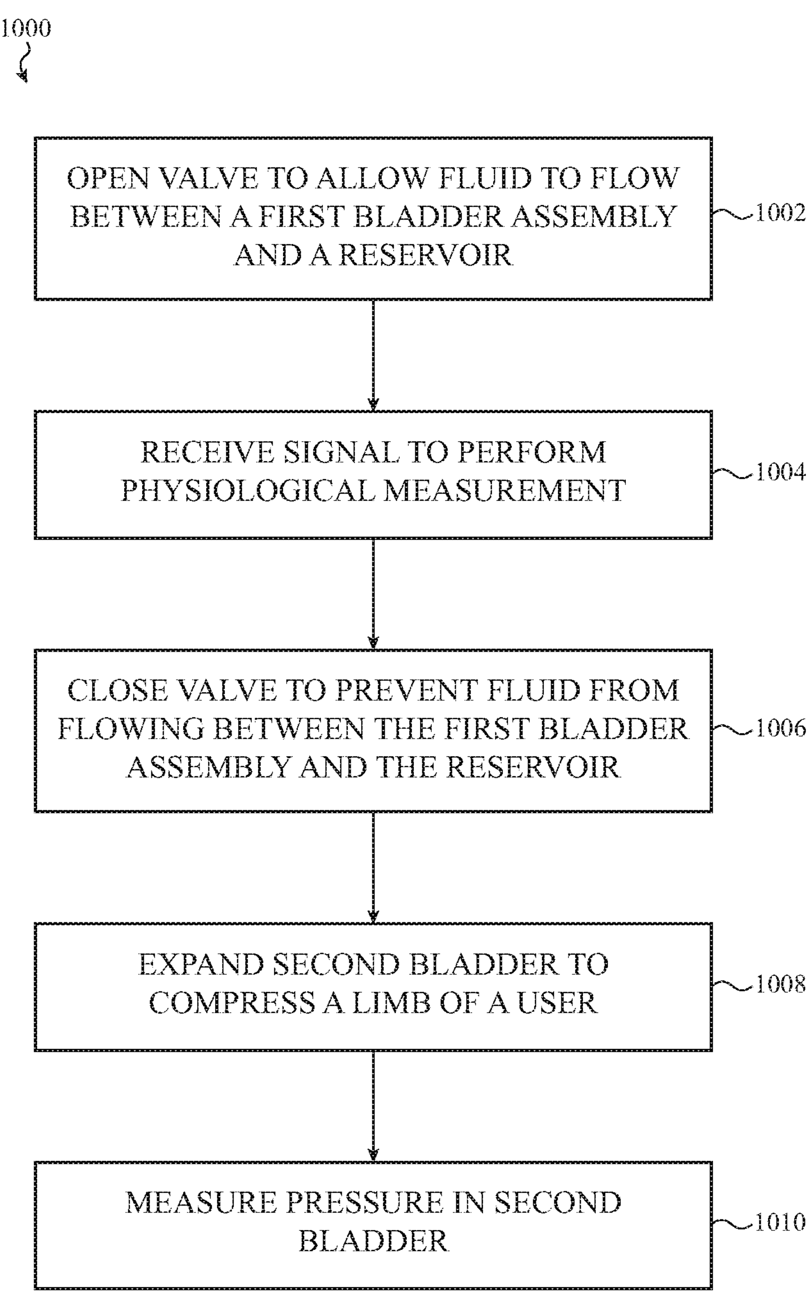
FIG. 10 illustrates an example method of operating a blood pressure measurement device.

FIG. 10 illustrates an example method 1000 of operating a blood pressure measurement device. The method 1000 can be performed using the blood pressure measurement device described herein, or using one or more components of that device such as the cuff, bladder assembly, reservoir and valve. At 1002, the valve may be opened to allow fluid to flow between a first bladder assembly and a reservoir. At 1004, a processer of the blood pressure measurement device may receive a signal to perform a blood pressure measurement on a user wearing the device. At 1006, the processor can cause the valve to close to prevent fluid from moving between the expandable bladder assembly and the reservoir. At 1008, the processor can cause the measurement bladder to expand to compress the limb of a user. At 1010, the processor may measure the pressure in the second bladder at various levels of compression to determine a blood pressure of a user.

Figure 11:
FIG. 11 Illustrates an example block diagram of blood pressure measurement device.
Figure 11:
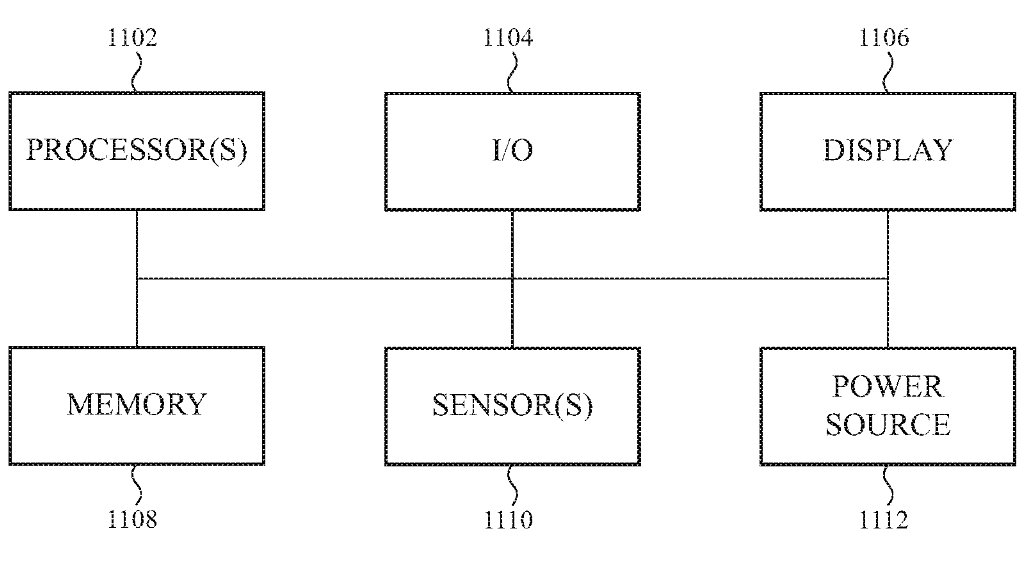

FIG. 11 illustrates an example block diagram of blood pressure measurement device 1100, which may in some cases take the form of any of the blood pressure measurement devices 1100 or components thereof described with reference to FIGS. 1-10. blood pressure measurement device 1100, can include a processor 1102, an input/output (I/O) mechanism 1104 (e.g., an input/output device, such as a touch screen, crown or button, input/output port, or haptic interface), a display 1106 (e.g., a light emitting display), memory 1108, sensors 1110 (e.g., pressure and auditory sensing systems), and a power source 1112 (e.g., a rechargeable battery). The processor 1102 can control some of all of the operations of the blood pressure measurement device 1100. The processor 1102 can communicate, either directly or indirectly, with some or all of the components of the electronic device 1100. For example, a system bus or other communication mechanism 1114 can provide communication between the processor 1102, the I/O mechanism 1104, the display 1106, the memory 1108, the sensors 1110, and the power source 1112.

The processor 1102 can be implemented as any electronic device capable of processing, receiving, or transmitting data or instructions. For example, the processor 1102 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 1100 can be controlled by multiple processors. For example, select components of the electronic device 1100 (e.g., a sensor 1110) may be controlled by a first processor and other components of the electronic device 1100 (e.g., the display 1106) may be controlled by a second processor, where the first and second processors may or may not be in communication with each other.

The I/O mechanism 1104 can transmit and/or receive data from a user or another electronic device. An I/O device can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The memory 1108 can store electronic data that can be used by the electronic device 1100. For example, the memory 1108 can store electrical data or content such as, for example, audio and video files, documents and applications, device settings and user preferences, timing signals, control signals, and data structures or databases. The memory 1108 can be configured as any type of memory. By way of example only, the memory 1108 can be implemented as random access memory, read-only memory, Flash memory, removable memory, other types of storage elements, or combinations of such devices.

The electronic device 1100 may also include one or more sensors 1110 positioned almost anywhere on the electronic device 1100. The sensor(s) 1110 can be configured to sense one or more type of parameters, such as but not limited to, pressure, sound, light, touch, heat, movement, relative motion, biometric data (e.g., biological parameters), and so on. For example, the sensor(s) 1110 may include a pressure sensor, an auditory sensor, a heat sensor, a position sensor, a light or optical sensor, an accelerometer, a pressure transducer, a gyroscope, a magnetometer, a health monitoring sensor, and so on. Additionally, the one or more sensors 1110 can utilize any suitable sensing technology, including, but not limited to, capacitive, ultrasonic, resistive, optical, ultrasound, piezoelectric, and thermal sensing technology.

The power source 1112 can be implemented with any device capable of providing energy to the electronic device 1100. For example, the power source 1112 may be one or more batteries or rechargeable batteries. Additionally or alternatively, the power source 1112 can be a power connector or power cord that connects the electronic device 1100 to another power source, such as a wall outlet.

As described above, one aspect of the present technology is directed to techniques for a blood pressure measurement device and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A cuff for measuring blood pressure of a user, comprising:

a cuff configured to wrap at least partially around a limb of the user;

a measurement bladder configured to restrict blood flow through the limb of the user when measuring blood pressure of the user;

a pump fluidly coupled to the measurement bladder;

a pressure sensor configured to measure pressure within the measurement bladder when measuring the blood pressure of the user;

a bladder assembly coupled with the cuff, configured to retain a fluid within an internal chamber and maintain a circumferential dimension when a volume of the fluid within the internal chamber is held constant, the bladder assembly comprising:

a cell defining at least a portion of the internal chamber; and a fluid passage in fluid communication with the cell;

a reservoir coupled with the fluid passage and configured to exchange the fluid with the bladder assembly; and a valve configured to control the exchange of the fluid between the bladder assembly and the reservoir; wherein:

the bladder assembly, the reservoir, and the valve are isolated from the measurement bladder and the pump;

the bladder assembly is configured to:

increase in length when a volume of the fluid in the internal chamber decreases; and decrease in length when the volume of the fluid in the internal chamber increases; and when measuring the blood pressure of the user, the valve is configured to prevent movement of fluid between the bladder assembly and the reservoir such that the volume of the fluid within the chamber is held constant and the pump is operated to inflate the measurement bladder.

2. The cuff of claim 1, wherein:

the cell is a first cell;

the portion is a first portion;

the cuff further comprises a second cell in fluid communication with the first cell and defining a second portion of the internal chamber;

the bladder assembly comprises:

a top sheet; and a bottom sheet joined with the top sheet;

the first cell is a first elongated tube;

the second cell is a second elongated tube;

the first elongated tube and second elongated tubes are both formed by coupling sections of the top sheet to the bottom sheet;

the fluid passage is defined by the top and bottom sheets.

3. The cuff of claim 1, wherein:

the valve is configured to switch between:

a first state in which the fluid can move between the bladder assembly and the reservoir; and a second state that prevents the fluid from moving between the bladder assembly and the reservoir.

4. The cuff of claim 3, further comprising a housing coupled to the bladder assembly, wherein the reservoir and the valve are located within the housing.

5. The cuff of claim 1, wherein the reservoir comprises an elastic member that is configured to increase or maintain a pressure of the fluid as the volume of the fluid in the reservoir increases.

6. The cuff of claim 1, wherein:

the cell is a first cell;

the portion is a first portion;

the cuff further comprises a second cell;

the first cell defines a first elongated tube;

the second cell defines a second elongated tube; and the first and second elongated tubes are configured to extend along a length of a limb of the user when the cuff is worn by the user.

7. The cuff of claim 1, wherein the bladder assembly comprises:

a top sheet; and a bottom sheet joined to the top sheet to define the cell, and the fluid passage.

8. The cuff of claim 7, wherein the bottom sheet is joined to the top sheet at defined locations such that the top sheet and the bottom sheet are substantially inseparable at the defined locations.

9. The cuff of claim 1, wherein:

the cell is a first cell;

the bladder assembly further defines a second cell;

the bladder assembly comprises first and second edges; and the bladder assembly defines relief features in each of the first and second edges that separate the first and second cells.

10. A wearable cuff, comprising:

a measurement bladder configured to restrict blood flow through the limb of the user when measuring blood pressure of the user;

a pump fluidly coupled to the measurement bladder and operable to inflate the measurement bladder when measuring the blood pressure of the user;

a pressure sensor configured to measure pressure within the measurement bladder when measuring the blood pressure of the user;

a bladder assembly configured to contain a fluid, and defined by:

an outer component that is liquid impermeable and defines a series of expandable channels; and an inner component and formed from a fluid permeable material that has a lower compliance than the outer component; and a reservoir coupled with the bladder assembly and configured to exchange the fluid with the bladder assembly; wherein:

the bladder assembly and the reservoir are isolated from the measurement bladder and the pump;

the bladder assembly is configured to:

increase in length when a volume of the fluid within the bladder assembly decreases; and decrease in length when the volume of the fluid within the bladder assembly increases.

11. The wearable cuff of claim 10, wherein:

the outer component is formed from a first sheet joined with a second sheet; and the inner component is positioned between the first sheet and the second sheet.

12. The wearable cuff of claim 10, wherein the inner component is configured to bias the bladder assembly toward a contracted state in which the length of the bladder assembly is decreased.

13. The wearable cuff of claim 12, wherein the inner component is formed from an elastic material that is coupled to the outer component.

14. The wearable cuff of claim 10, wherein:

the outer component defines first and second edges; and the outer component comprises relief features extending along the first and second edges.

15. The wearable cuff of claim 14, wherein the relief features are defined by a series of recesses formed along the first and second edges of the outer component.

16. The wearable cuff of claim 14, wherein the relief features increase a range of motion of the bladder assembly.

17. A wearable blood pressure measuring device, comprising:

a cuff defining an interior surface that at least partially wraps around a user's limb;

a first bladder assembly coupled with the cuff and defining a chamber that is configured to:

contain a fluid; and maintain a circumferential dimension when a volume of the fluid within the chamber is held constant;

a reservoir configured to exchange the fluid with the first bladder assembly;

a valve configured to control the exchange of the fluid between the first bladder assembly and the reservoir;

a second bladder assembly positioned along a portion of the interior surface and configured to inflate and deflate to restrict blood flow through the user's limb when a user's blood pressure is measured; and a pump and fluidly coupled to the second bladder assembly;

wherein:

the first bladder assembly and the reservoir are isolated from the second bladder assembly and the pump;

in response to measuring the user's blood pressure, the valve prevents movement of fluid between the first bladder assembly and the reservoir such that the volume of the fluid within the chamber is held constant and the pump is operated to inflate the second bladder assembly.

18. The wearable blood pressure measuring device of claim 17, wherein when the user's blood pressure is not being measured, the valve allows movement of fluid between the first bladder assembly and the reservoir.

19. The wearable blood pressure measuring device of claim 18, wherein the first bladder assembly is further configured to expand and contract non-uniformly when the valve allows movement of fluid between the first bladder assembly and the reservoir.

20. The wearable blood pressure measuring device of claim 17, wherein the first bladder assembly comprises:

a top sheet comprising a substantially inextensible material; and a bottom sheet comprising an elastic material and coupled to the top sheet.

* * * * *